United States Patent [19]

Sarges

[11] Patent Number: 4,623,728

[45] Date of Patent: Nov. 18, 1986

[54] INTERMEDIATES FOR 1,3-DISUBSTITUTED PIPERIDINE COMPOUNDS AS NEUROLEPTIC AGENTS

[75] Inventor: Reinhard Sarges, Mystic, Conn.

[73] Assignee: Pfizer Inc., New York, N.Y.

[21] Appl. No.: 829,634

[22] Filed: Feb. 14, 1986

Related U.S. Application Data

[62] Division of Ser. No. 634,910, Jul. 26, 1984, Pat. No. 4,593,037.

[51] Int. Cl.$^4$ .................................... C07D 211/22
[52] U.S. Cl. .................................... 546/236
[58] Field of Search ........................ 549/236

[56] References Cited

U.S. PATENT DOCUMENTS 4,072,685 2/1978 Nedelec et al. ............... 546/240
4,241,071 12/1980 Martin et al. ................. 546/240
4,332,942 6/1982 Althuis et al. ................ 546/240

FOREIGN PATENT DOCUMENTS 8101552 6/1981 PCT Int'l Appl. .
984119 2/1965 United Kingdom .

OTHER PUBLICATIONS

Julia et al., Bulletin de la Societe Chimique de France, No. 3, pp. 1000–1007 (1968).
Hacksell et al., Journal of Medicinal Chemistry, 24, pp. 1475–1482 (1981).

Primary Examiner—Norma S. Milestone
Attorney, Agent, or Firm—Charles J. Knuth; Peter C. Richardson; J. Trevor Lumb

[57] ABSTRACT

Certain novel 1-(substituted-alkyl)-3-(3-hydroxyphenyl)piperidine compounds, and the pharmeceutically-acceptable acid-addition salts thereof, possess pharmaceutical activity as neuroleptic agents, and they are useful for treating psychotic disorders, e.g. schizophrenia, in human subjects. In particular, they are useful for alleviating such symptoms as anxiety, agitation, excessive aggression, tension and social or emotional withdrawal in psychotic patients.

Certain 3-(3-methoxyphenyl)piperidine compounds are useful as chemical intermediates to the aforementioned neuroleptic agents.

2 Claims, No Drawings

INTERMEDIATES FOR 1,3-DISUBSTITUTED PIPERIDINE COMPOUNDS AS NEUROLEPTIC AGENTS

This is a division of application Ser. No. 634,910 filed July 26, 1984, now U.S. Pat. No. 4,593,037.

BACKGROUND OF THE INVENTION

Certain members of the human population suffer from mental disorders known as psychoses, and such individuals exhibit abnormal perceptual and behavioral characteristics. Attempts have been made to develop a biochemical explanation for psychoses, and these attempts have focussed on the possible role of certain substances found in the brain and known as biogenic amines (e.g. dopamine). In particular, the possible importance of chemical imbalances among these biogenic amines has been studied.

On the other hand, it has been known for several years that in some cases it is possible to alleviate the symptoms of psychotic disorders by the administration of certain chemical substances known as antipsychotic, ataractic or neuroleptic agents. Both naturally-occurring substances and chemically synthesized agents have been used in this regard. For example, extracts from the shrub Rauwolfia serpentina have long been used in Hindu medicine, and a constituent of these extracts, the alkaloid reserpine, has been shown to have antipsychotic properties. Two, well-known classes of synthetic compounds which have found use in clinical medicine for the drug therapy of psychoses are phenothiazines, e.g. chlorpromazine, and butyrophenones, e.g. haloperidol.

However, no single compound has been found which is ideally suited for the treatment of all psychoses; consequently, the search for new antipsychotic agents continues.

Accordingly, it is an object of the present invention to provide a new series of chemical compounds which are of value in the treatment of psychoses. More particularly, these new chemical compounds are piperidine derivatives, having a phenylalkyl group at the 1-position and a 3-hydroxyphenyl group at the 3-position, and optionally having further substituents.

Julia et al., Bull. Soc. Chim. France, 3, 1000 (1968) have reported the preparation of a series of 3-phenylpiperidines, including 1-(2-phenylethyl)-3-(3-hydroxyphenyl)piperidine, and the latter compound has been shown to have dopamine-autoreceptor stimulating activity (Hacksell et al., J. Med. Chem., 24, 1475 [1981]). Published PCT patent application No. 81/01552 discloses a series of 1-substituted-3-(3-hydroxyphenyl)-piperidines as dopamine-autoreceptor agonists.

SUMMARY OF THE INVENTION

This invention provides novel 1,3-disubstituted piperidine compounds of the formula

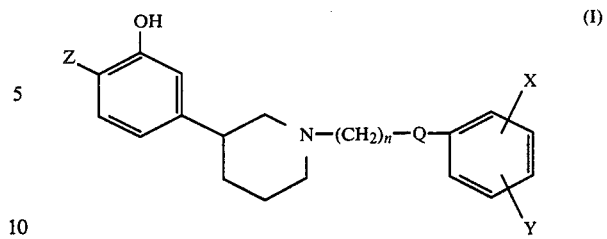

and the pharmaceutically-acceptable acid-addition salts thereof; wherein
X and Y are each hydrogen, fluoro, chloro or bromo;
Z is hydrogen, fluoro or chloro;
Q represents a chemical bond, a divalent group of the formula —C(=O)— or a divalent group of the formula —CH(OH)—;
and n is an integer from 3 to 5.

Said compounds of the formula I are active as neuroleptic agents, and they are useful for the treatment of psychotic disorders in human subjects. In particular they are of value in treating psychoses of the schizophrenic types.

Accordingly, this invention also provides a method of treating a psychotic disorder in a human subject using a compound of formula I, wherein X, Y, Z, Q and n are as defined previously; and also pharmaceutical compositions which comprise a compound of formula I, wherein X, Y, Z, Q and n are as previously defined, and a pharmaceutically-acceptable carrier.

A preferred group of compounds of this invention consists of the compounds of formula I, wherein X and Y are each hydrogen and Q represents a chemical bond. Within this preferred group, particularly preferred compounds are those wherein Z is hydrogen and n is 3.

A second preferred group of compounds of this invention consists of the compounds of formula I, wherein X is 4-fluoro, Y is hydrogen and Q represents —C(=O)— or —CH(OH)—. Within this second preferred group, particularly preferred compounds are those wherein Z is hydrogen and n is 3.

An especially preferred individual compound of this invention is (R)(+)-1-(3-phenylpropyl)-3-(3-hydroxyphenyl)piperidine, the dextrorotatory isomer of a compound of formula I, wherein X, Y and Z are each hydrogen, Q represents a chemical bond and n is 3.

DETAILED DESCRIPTION OF THE INVENTION

The neuroleptic compounds of this invention of the formula I, wherein X, Y, Z and n are as defined previously, and Q is a chemical bond or —C(=O)—, can be prepared from the corresponding phenolic ether of the formula:

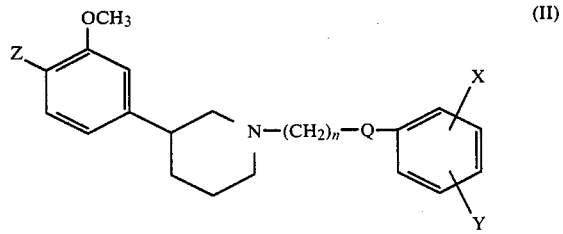

This is a classical demethylation reaction of an aromatic methoxy group, and it can be carried out using standard reagents for this type of transformation. Thus, typical reagents which can be used are hydrogen bromide, hydrogen iodide (optionally in the presence of red phosphorus), potassium iodide in concentrated phosphoric acid, pyridine hydrochloride and boron tribromide. However, a preferred reagent is hydrogen bromide, especially hydrogen bromide in water, acetic acid, or mixtures thereof. A particularly convenient form of hydrogen bromide is 48% hydrobromic acid, i.e. the constant-boiling solution in water.

Conversion of the phenolic ether II into said compound of formula I can be carried out by treating the ether of formula II with at least one molar equivalent of hydrogen bromide, at a temperature in the range from 100° to 160° C., and usually at about 125° C., in an inert solvent. An inert solvent is one which will dissolve the starting material to an appreciable extent; and which does not adversely interact with either the starting material or the product. Water and acetic acid, and mixtures thereof, are convenient solvents. In practice, a large excess of hydrogen bromide, e.g. from about 10 to about 100 equivalents, is commonly used. Typically, the compound of formula II is heated under reflux in a mixture of 48% hydrobromic acid and glacial acetic acid for several hours, e.g. from 2 to 10 hours, until cleavage of the ether linkage is substantially complete.

The product can be isolated by standard procedures. Usually, at the end of the reaction, the reaction mixture is diluted with an excess of water and then basified, e.g. with an alkali, such as sodium hydroxide or sodium carbonate, and then the product is extracted into a volatile, water-immiscible, organic solvent, such as ethyl acetate. The product can then be recovered from the organic solvent by evaporation. The recovered product can be purified by standard methods, such as recrystallization and chromatography.

The compounds of formula II, wherein X, Y, Z and n are as defined previously, and Q is a chemical bond or —C(=O)—, can be prepared from the approximate 3-phenylpiperidine compound of the formula

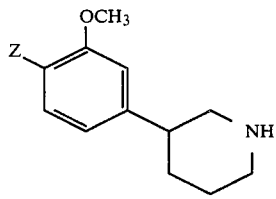

For preparation of said compound of formula II, wherein Q represents a chemical bond, from a compound of formula III, a conventional technique involves acylating the appropriate compound of formula III with the requisite carboxylic acid or activated derivative thereof of formula

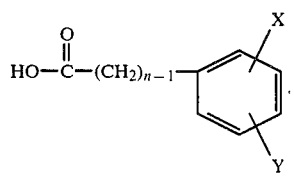

to give the amide of the formula

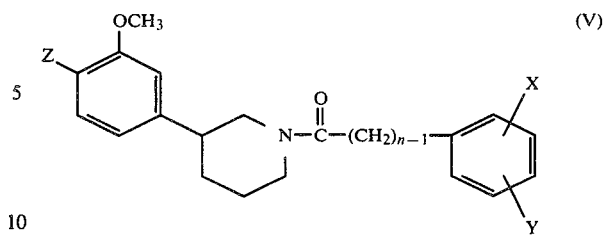

followed by reduction of the newly-formed amide moiety, wherein X, Y, Z and n are as defined previously.

Conversion of the amine (III) into the amide (V) is usually carried out by reaction with an activated derivative of the acid of formula IV in a reaction-inert solvent, according to standard procedures. However, a convenient activated derivative of the acid of formula IV is the acid chloride. In this case, the amine of formula III is usually contacted with one equivalent, or a slight excess, of the acid chloride of the acid of the formula IV, in a reaction-inert solvent, at a temperature of from about −20° to 30° C., in the presence of an acid-binder. A reaction-inert solvent is one which will dissolve the starting materials to a significant extent, and does not adversely interact with either the starting materials or the product. A solvent having sufficient volatility that it can be removed by evaporation is usually used. Typical solvents which can be used are hydrocarbons, such as benzene and toluene; chlorinated hydrocarbons, such as dichloromethane, chloroform and 1,2-dichloroethane; ethers, such as tetrahydrofuran and 1,2-dimethoxyethane; low-molecular weight ketones, such as acetone and methyl isobutyl ketone; acetonitrile; and mixtures of these solvents. Typical acid-binders which can be used are tertiary amines, such as triethylamine, tributylamine, diisopropylethylamine, pyridine, 4-(N,N-dimethylamino)pyridine, N,N-dimethylaniline, and the like, and the acid-binder is normally present in a molar amount equivalent to the acid chloride. The rate of the acylation reaction varies with the reaction temperature, the concentration of the reagents and the structures of the individual reagents, but normally the reaction proceeds quite quickly. At about 0° C., reaction times of a few minutes up to a few hours, e.g. two hours, are commonly used. At the end of the reaction, the amide of formula V can be isolated in conventional fashion. For example, when a water-immiscible solvent is used, such as a hydrocarbon solvent, the hydrochloride salt of the acid binder is removed by filtration or washing with water, and the amide product is recovered by evaporation of the solvent. Alternatively, when a water-miscible solvent is used, the reaction mixture can be diluted with an excess of water and the amide can be extracted into a volatile, water-immiscible, organic solvent at an acidic or neutral pH. Evaporation of the organic extracts then affords the required amide.

The amide of formula V can be purified by standard means, such as recrystallization or chromatography, if desired. On the other hand, the crude amide is normally satisfactory for direct reduction to the compound of formula II.

Conversion of the amide of formula V into the corresponding compound of formula II is accomplished by reduction of the >N—C(=O)— linkage into a >N—CH₂— linkage. A variety of reagents known in the art for this type of transformation can be used, but, in the present instance, reduction with lithium aluminum hydride according to standard procedures is commonly used.

Reduction of the amide of formula V with lithium aluminum hydride is usually carried out by contacting the amide with an excess, e.g. a two- to ten-fold excess, of lithium aluminum hydride in an aprotic solvent, such as an ether. Typical ether solvents which can be used are diethyl ether, diisopropyl ether, 1,2-dimethoxyethane, di(2-methoxyethyl)ether, tetrahydrofuran and dioxane, and the reaction is normally carried out from about room temperature (e.g. 20° C.) up to about 80° C. Reaction times from about 30 minutes up to a few hours, e.g. three hours, are usually sufficient for complete reduction. Any excess reducing agent is then decomposed by the cautious addition of water, and the product can be recovered by evaporation of the solvent after removal of the inorganic byproducts (lithium and aluminum salts) by standard methods.

The compounds of formula II, wherein Q is a divalent group of the formula —C(=O)—, can be prepared from the appropriate of the formula III by alkylation using a compound of the formula

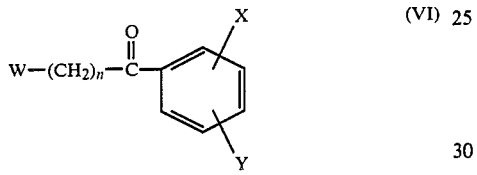

wherein W is a good leaving group. Typical groups for W are chloro, bromo, iodo, lower-alkylsulfonyloxy, phenylsulfonyloxy and tolylsulfonyloxy. A preferred group for W is chloro.

Alkylation of an amine of the formula III with a compound of the formula VI, wherein W is chloro, is usually carried out by contacting the amine with from about one to three molar equivalents of the chloro compound in an inert solvent, such as a low-molecular weight ketone (e.g. acetone or methyl isobutyl ketone) at the reflux temperature of the solvent, in the presence of an excess of an acid scavenger, such as potassium carbonate. The reaction normally takes several hours, e.g. from 12 to 60 hours, to reach completion. The reaction mixture is then diluted with a large excess of water, and the product is extracted into a volatile, water-immiscible, organic solvent, such as ethyl acetate. Evaporation of the organic extract then provides the compound of formula II, wherein Q is —C(=O)—.

A compound of formula II can be purified by conventional methods such as recrystallization or chromatography, if desired; alternatively, it can be used directly for conversion into the corresponding neuroleptic agent of formula I.

The compounds of this invention of the formula I, wherein X, Y, Z and n are as defined previously, and Q represents a divalent group of the formula —CH(OH)—, can be prepared from the corresponding compound of the formula I, wherein Q is —C(=O)—. A variety of agents known for the reduction of ketones to secondary alcohols can be used for this purpose, but a particularly convenient reagent in the present case is sodium borohydride. When using sodium borohydride, a mixture of the compound of formula I, wherein Q is —C(=O)—, and an excess of sodium borohydride in a lower-alkanol solvent, e.g. methanol, are usually stored at a temperature from 0° to 30° C., and preferably about 25° C., until the reduction is complete. The reaction normally proceeds relatively rapidly, but often it is continued for several hours, e.g. from 5 to 20 hours. The methanol solvent is then removed by evaporation in vacuo, and the residue is partitioned between water and a volatile, water-immiscible, organic solvent. Separation of the layers and evaporation of the organic layer affords the required compound of the formula I, wherein Q is —CH(OH)—. If desired, the latter compound can be purified by methods known in the art, such as recrystallization or chromatography.

The piperidine compounds of the formula III can be prepared from the corresponding pyridine compound of the formula

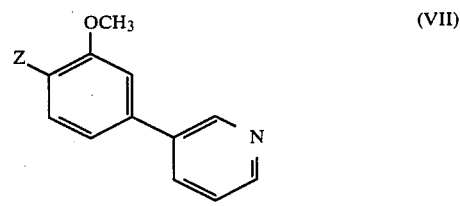

wherein Z is hydrogen, fluoro or chloro, by reduction. This reduction is conveniently carried out by hydrogenation, using a platinum catalyst, in methanol containing concentrated hydrochloric acid. See further, Hacksell et al., Journal of Medicinal Chemistry, 24, 1475 (1981).

The pyridine compounds of formula VII can be prepared by coupling 3-bromopyridine with the Grignard reagent of formula IX, which in turn is obtained from the corresponding bromo compound of formula VIII:

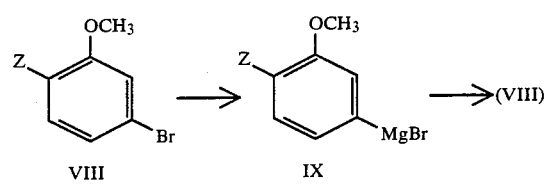

wherein Z is hydrogen, fluoro or chloro. The bromo compound VIII is converted into the Grignard reagent IX by reaction with magnesium turnings, in tetrahydrofuran, under standard conditions, and the coupling of the Grignard reagent with 3-bromopyridine can be carried out in the same solvent and can be catalysed by either dichlorobis(triphenylphosphine)nickel(II) or tetrakis(triphenylphosphine)palladium(O). Hacksell et al., Journal of Medicinal Chemistry, 24, 1475 (1981), and references cited therein.

The bromo compounds of the formula VIII are either known compounds, which can be prepared by the known methods, or they can be prepared by standard transformations, well-known in the art, from known compounds. For example, they can be prepared from the appropriate amino-anisole of formula X by diazotization followed by treatment with cuprous bromide, viz:

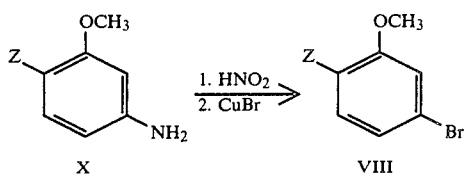

The neuroleptic agents of this invention of formula I and the intermediate compounds of the formula III are basic, and they will form acid-addition salts. All such salts are within the scope of this invention; however, when it is intended to use a compound of formula I as a neuroleptic agent in a human patient, it is necessary to use a non-toxic, i.e. pharmaceutically-acceptable, salt.

The salts of the compounds of formulae I and III can be prepared in conventional fashion. For example, the compound of formula I or III is combined with a stoichiometric amount of the appropriate acid in an inert solvent, and then the salt is recovered by solvent evaporation, by filtration if it precipitates spontaneously, or by precipitation by a non-solvent followed by filtration. Typical salts which can be formed include hydrochloride, hydrobromide, sulfate, nitrate, phosphate, citrate, tartrate, pamoate, methanesulfonate, benzenesulfonate, naphthalenesulfonate and toluenesulfonate salts.

As will be appreciated by one skilled in the art, in a compound of formula I, the 3-position on the piperidine ring and the group Q when it is a divalent group of the formula —CH(OH)— both represent asymmetric centers. This leads to the existence of several isomers of the compounds of the formula I. Moreover, all the individual isomers of the compounds of formula I, and all mixtures of such isomers, are within the scope and purview of this invention.

Preparation of a compound of the formula I, wherein Q represents a chemical bond or a divalent group of the formula —C(=O)—, from a racemic compound of the formula III by the method described hereinbefore leads to the compound I as a racemic mixture, consisting of two optical isomers or enantiomers. Such a racemic mixture can be separated into its optical isomers or enantiomers by the classical method of optical resolution involving salt formation with an optically-active acid. Alternatively, the individual enantiomers of a compound of formula I, wherein Q is a chemical bond or —C(=O)—, can be prepared by starting with an optically-pure compound of formula III, since the configuration at the 3-position of the piperidine ring is unaffected during the sequence: compound III to compound II to compound I.

A racemic compound of formula III can also be resolved into its enantiomers by salt formation with an optically-active acid followed by separation of the diastereomers, followed by regeneration of the parent amine. However, a particularly convenient method for obtaining the optical antipodes of a compound of the formula III involves the sequence: (a) acylation of a racemic compound of the formula III with an enantiomerically-pure acid chloride of 2-methoxy-2-phenyl-2-trifluoromethylacetic acid; (b) chromatographic separation of the mixture of diastereomers thus obtained; and (c) hydrolysis of the individual diastereomers to give the individual enantiomers of the compound of the formula III. Methods for obtaining an enantiomerically-pure acid chloride of 2-methoxy-2-phenyl-2-trifluoromethylacetic acid are taught by Dale et al., *Journal of Organic Chemistry*, 34, 2543 (1969).

Reduction of an optically-pure compound of the formula I, wherein Q is —C(=O)—, using sodium borohydride leads to a mixture of two optically-active diastereomers of the formula I, wherein Q is —CH(OH)—, which can be separated by such methods as chromatography. Correspondingly, reduction of a racemic compound of formula I, wherein Q is —C(=O)—, with sodium borohydride leads to a mixture of two racemates, wherein Q is —CH(OH)—. The latter mixture can be separated into the individual racemates by chromatography. The individual racemates themselves can be resolved into their constituent enantiomers by the classical method of salt formation with an optically-active acid.

As indicated hereinbefore, the compounds of formula I, wherein X, Y, Z, Q and n are as defined previously, and the pharmaceutically-acceptable acid-addition salts thereof, are active as neuroleptic agents. In particular, they show the ability to antagonize amphetamine-induced stereotypy in mice, and such ability can be demonstrated by methods based on standard procedures. For example, in one method, groups of five mice (Charles River males, Swiss CD strain, 20-25 g in weight) which have been fasted for 18 hours, but with water available ad lib., are treated first with the test compound in a suitable vehicle and then, one hour later, with dextroamphetamine sulfate, 20 mg/kg intraperitoneally. Immediately after amphetamine treatment, the mice are placed in a transparent plastic cubicle, 6×7×7 cm, with a paper floor-covering, and 1 hour after amphetamine administration they are observed for the magnitude of the amphetamine-induced stereotypy. Since the dose of anphetamine used is sufficient to cause symptoms in otherwise untreated mice similar to those reported for rats by Weissman et. al. (*J. Pharmacol. Exp. Ther.* 151, 339 [1961]), a similar 5-point scoring scale is used as follows: 0 =sleeping; 1=alert, but not moving; 2=moving around cubicle; 3=sniffing, usually directed upward at the top of the cubicle; 4=licking the wall or floor of the cubicle, or gnawing or biting the floor or wall of the cubicle. In general, a test compound which receives a score of 0 or 1 is considered very active, a compound scoring 2 is considered moderately active, and a compound scoring 3 or 4 is considered inactive. Control groups are run in which the mice receive the test vehicle and the amphetamine treatment only. Mice in these groups normally achieve a score of 3 or 4.

The neuroleptic activity of the compounds of this invention makes them useful for treating psychotic disorders in human subjects. For example, these compounds are useful for treating psychotic disorders of the schizophrenic types, and in particular the compounds are useful for removing or ameliorating such symptoms as anxiety, agitation, excessive agression, tension, and social or emotional withdrawal in psychotic patients.

A neuroleptic compound of formula I, or a pharmaceutically-acceptable salt thereof, can be administered to a human subject either alone, or, preferably, in combination with pharmaceutically-acceptable carriers or diluents, in a pharmaceutical composition, according to standard pharmaceutical practice. A compound can be administered orally or parenterally. Parenteral administration includes especially intravenous and intramuscular administration. Additionally, in a pharmaceutical composition comprising a compound of formula I, or a pharmaceutically-acceptable salt thereof, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use of a neuroleptic agent of this invention, the compound can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When a neuroleptic agent of this invention is to be used in a human subject to treat a psychotic disorder, the daily dosage will normally be determined by the prescribing physician. Moreover, the dosage will vary according to the age, weight and response of the individual patient, as well as the severity of the patient's symptoms. However, in most instances, an effective amount for treating a psychotic disorder will be a daily dosage in the range from 1 to 500 mg, and preferably 5 to 100 mg, in single or divided doses, orally or parenterally. In some instances it may be necessary to use dosages outside these limits.

The following examples are being provided solely for the purpose of further illustration.

EXAMPLE 1

1-(3-Phenylpropyl)-3-(3-hydroxyphenyl)piperidine

To a stirred solution of 15.2 g (0.049 mole) of 1-(3-phenylpropyl)-3-(3-methoxyphenyl)piperidine from Preparation 1 in 75 ml of glacial acetic acid was added 150 g of 48% aqueous hydrobromic acid. The reaction mixture was heated at 120° C. for 2.5 hours and then it was poured onto ice. The resulting mixture was basified with sodium carbonate and then it was extracted with ethyl acetate. The extracts were washed with water, followed by sodium chloride solution, and then they were dried and evaporated to give 17.2 g of crude product as a tan solid. Purification by recrystallization from a mixture of ethyl acetate/hexane/triethylamine (5:5:0.5) gave 4.0 g (28%) of the title compound, m.p. 119°–120° C.

Analysis: Calcd. for $C_{20}H_{25}NO$: C, 81.31; H, 8.53; N, 4.74%. Found: C, 81.71; H, 8.59; N, 4.80%.

EXAMPLE 2

By treatment of the products of Preparation 2 with 48% aqueous hydrobromic acid, using the procedure of Example 1, the following compounds can be prepared:

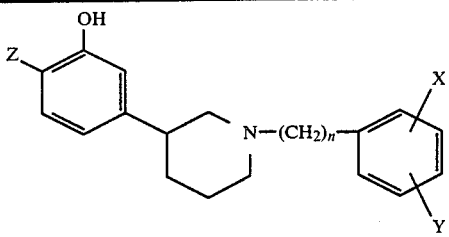

| Z  | n | X    | Y    |
|----|---|------|------|
| H  | 4 | H    | H    |
| H  | 5 | H    | H    |
| H  | 3 | 4-Cl | H    |
| H  | 3 | 3-Br | H    |
| H  | 4 | 2-F  | H    |
| F  | 3 | 3-Cl | H    |
| Cl | 3 | 4-F  | H    |
| H  | 4 | 3-Cl | 5-Cl |
| H  | 5 | 2-F  | 4-F  |
| H  | 3 | 3-F  | 4-Cl |

EXAMPLE 3

(S)(−)-1-(3-Phenylpropyl)-3-(3-hydroxyphenyl)piperidine Hydrobromide

A mixture of 1.8 g (5.8 mmole) of the (S)-1-(3-phenylpropyl)-3-(3-methoxyphenyl)piperidine from Preparation 3, 16 ml of 48% aqueous hydrobromic acid and 8 ml of glacial acetic acid was heated at 120° C. for 4 hours. The reaction mixture was then poured onto ice. The resulting mixture was basified with potassium carbonate and then it was extracted with ethyl acetate. The extracts were washed with water, followed by saturated sodium chloride, and then dried (MgSO$_4$) and evaporated in vacuo. The residue was chromatographed on 150 ml of silica gel, eluting with chloroform/methanol (95:5). The product-containing fractions were combined and evaporated in vacuo to give 930 mg of an oil. The oil was diluted with 20 ml of diethyl ether and the insoluble material was removed by filtration and discarded. The filtrate was saturated with gaseous hydrogen bromide and then it was concentrated in vacuo. The residue was dissolved in 10–20 ml of acetonitrile, and to the solution thus obtained was added diethyl ether until the solution became cloudy. The solid which formed was then collected by filtration to give 150 mg of the title compound, m.p. 181°–183° C., $[\alpha]_D^{25} = -10.1°$ (c=1; $C_2H_5OH$).

Analysis: Calcd. for $C_{20}H_{25}NO\cdot HBr$:
C, 63.83; H, 6.96; N, 3.72%.
Found: C, 63.92; H, 6.78; N, 3.94%.

EXAMPLE 4

(R)(+)-1-(3-Phenylpropyl)-3-(3-hydroxyphenyl)piperidine Hydrobromide

The title compound was prepared in 16% yield from the (R)-1-(3-phenylpropyl)-3-(3-methoxyphenyl)piperidine from Preparation 4 by treatment with 48% aqueous hydrobromic acid in glacial acetic acid, using the procedure of Example 3. The product melted at 181°–183° C., $[\alpha]_D^{25} = +10.4°$ (c=1; $C_2H_5OH$).

Analysis: Calcd. for $C_{20}H_{25}NO\cdot HBr$: C, 63.83; H, 6.96; N, 3.72%. Found: C, 64.09; H, 6.96; N, 3.97%.

EXAMPLE 5

(−)-1-(3-Phenylpropyl)-3-(4-fluoro-3-hydroxyphenyl)-piperidine

The 1-(3-phenylpropyl)-3-(4-fluoro-3-methoxyphenyl)piperidine from Preparation 5 was reacted with 48% aqueous hydrobromic acid in glacial acetic acid using the procedure of Example 3. The product was chromatographed on silica gel, eluting with ethyl acetate/hexane/triethylamine (5:5:3). This afforded a 32% yield of the title compound, $[alpha]_D^{25} = -21.2°$ (c=1; $C_2H_5OH$).

Analysis: Calcd. for $C_{20}H_{24}FNO$: C, 76.64; H, 7.72; N, 4.47%. Found: C, 76.29; H, 7.83; N, 4.27%.

EXAMPLE 6

(+)-1-(3-Phenylpropyl)-3-(4-fluoro-3-hydroxyphenyl)-piperidine

The 1-(3-phenylpropyl)-3-(4-fluoro-3-methoxyphenyl)piperidine from Preparation 6 was reacted with 48% aqueous hydrobromic acid in glacial acetic acid using the procedure of Example 3. The product was chromatographed on silica gel, eluting with ethyl acetate/hexane/triethylamine (5:5:3). This afforded a 72% yield of the title compound, $[alpha]_D^{25} = +20.2°$ (c=1; $C_2H_5OH$).

Analysis: Calcd. for $C_{20}H_{24}FNO$: C, 76.64; H, 7.72; N, 4.47%. Found: C, 76.25; H, 7.46; N, 4.52%.

EXAMPLE 7

1-(4-Oxo-4-[4-fluorophenyl]butyl)-3-(3-hydroxyphenyl)piperidine

A mixture of 1.4 g (4 mmole) of 1-(4-oxo-4-[4fluorophenyl]butyl)-3-(3-methoxyphenyl)piperidine, 10 ml of 48% aqueous hydrobromic acid and 5 ml of glacial acetic acid was heated under reflux for ca. 20 hours. The reaction mixture was then poured onto a mixture of ice and water. The resulting mixture was basified with potassium carbonate and then it was extracted with ethyl acetate. The extracts were washed with water, followed by saturated sodium chloride solution, and then they were dried ($MgSO_4$) and evaporated in vacuo. The residue was purified by chromatography on 150 ml of silica gel, eluting with chloroform/methanol (95:5). The product was then recrystallized from chloroform to give 540 mg (30% yield) of the title compound as a chloroform solvate, m.p. 77°–78° C.

Analysis: Calcd. for $C_{21}H_{24}FNO_2 \cdot CHCl_3$: C, 57.34; H, 5.47; N, 3.04%. Found: C, 56.99; H, 5.28; N, 2.98%.

EXAMPLE 8

1-(4-Hydroxy-4-[4-fluorophenyl]butyl)-3-(3-hydroxyphenyl)piperidine

A mixture of 230 mg (5 mmole) of 1-(4-oxo-4-[4-fluorophenyl]butyl)-3-(3-hydroxyphenyl)piperidine and 193 mg (5 mmole) of sodium borohydride in 20 ml of methanol was stirred at room temperature overnight. The solvent was removed by evaporation in vacuo, and the residue was partitioned between ethyl acetate and water. The layers were separated, the aqueous phase was further extracted with ethyl acetate, and all the ethyl acetate phases were combined. The resulting ethyl acetate solution was washed with water, followed by saturated sodium chloride, and then it was dried ($MgSO_4$) and evaporated in vacuo. The residue was chromatographed on 150 ml of silica gel, eluting with chloroform/methanol (9:1). The product-containing fractions were combined and evaporated in vacuo to give 125 mg (67% yield) of the title compound as a foam, containing chloroform of solvation.

Analysis: Calcd. for $C_{21}H_{26}FNO_2 \cdot 0.25CHCl_3$: C, 68.37; H, 7.09; N, 3.75%. Found: C, 68.76; H, 7.24; N, 3.75%.

PREPARATION 1

1-(3-Phenylpropyl)-3-(3-methoxyphenyl)piperidine

To a stirred solution of 9.4 g (49.2 mmole) of 3-(3-methoxyphenyl)piperidine and 10.2 ml (73.8 mmole) of triethylamine in 120 ml of toluene, at 0° C., under nitrogen, was added dropwise, a solution of 12.4 g (73.8 mmole) of 3-phenylpropionyl chloride in 45 ml of toluene. The mixture was allowed to warm to room temperature, and then it was diluted with an equal volume of diethyl ether. The solid was removed by filtration and the filtrate was evaporated in vacuo to give 23.7 g of 1-(3-phenylpropionyl)-3-(3-methoxyphenyl)piperidine.

The 1-(3-phenylpropionyl)-3-(3-methoxyphenyl)piperidine was dissolved in 150 ml of dry tetrahydrofuran, and the solution was added to a suspension of 8.59 g (226 mmole) of lithium aluminum hydride in 150 ml of dry tetrahydrofuran, at room temperature. The resulting mixture was heated under reflux for 1 hour and then it was cooled in an ice-bath. To the cooled mixture was added, dropwise, with stirring, 43 ml of 3% aqueous sodium hydroxide, followed by 400 ml of diethyl ether. Stirring was continued for 45 minutes, and then the mixture was filtered. The filtrate was evaporated in vacuo to give 18.4 g of material.

PREPARATION 2

By acylation of 3-(3-methoxyphenyl)piperidine or the appropriate 3-(4-halo-3-methoxyphenyl)piperidine with the requisite acid chloride, followed by reduction with lithium aluminum hydride, using the procedure of Preparation 1, the following compounds can be prepared:

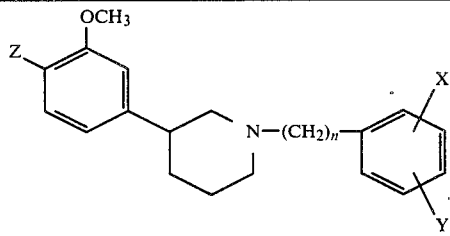

| Z  | n | X    | Y    |
|----|---|------|------|
| H  | 4 | H    | H    |
| H  | 5 | H    | H    |
| H  | 3 | 4-Cl | H    |
| H  | 3 | 3-Br | H    |
| H  | 4 | 2-F  | H    |
| F  | 3 | 3-Cl | H    |
| Cl | 3 | 4-F  | H    |
| H  | 4 | 3-Cl | 5-Cl |
| H  | 5 | 2-F  | 4-F  |
| H  | 3 | 3-F  | 4-Cl |

PREPARATION 3

(S)-1-(3-Phenylpropyl)-3-(3-methoxyphenyl)piperidine

To a stirred slurry of 1.0 g (5.2 mmole) of the (S)(+)-3-(3-methoxyphenyl)piperidine from Preparation 7, Part B, and 1 ml (7.8 mmole) of triethylamine in 10 ml of toluene, at 0° C., was added, dropwise, a solution of 1.3 g (7.8 mmole) of 3-phenylpropionyl chloride in 5 ml of toluene. The reaction mixture was then allowed to warm to room temperature and stirring was continued for 30 minutes. The reaction mixture was then filtered, and the filtrate was evaporated in vacuo to give a yellow oil. The yellow oil was dissolved in 15 ml of tetrahydrofuran and the resulting solution was added dropwise to a slurry of 910 mg (24 mmole) of lithium aluminum hydride in 15 ml of tetrahydrofuran. The resulting mixture was heated under reflux for 2 hours and then it was cooled in an ice-bath. To the cooled mixture was added, dropwise, with stirring, 5 ml of 3% sodium hydroxide, followed by 20 ml of diethyl ether. Stirring was continued for 15 minutes, and then the mixture was filtered. The filtrate was evaporated in vacuo. The residue was dissolved in toluene and evaporated in vacuo several times. This afforded 1.8 g of material.

PREPARATION 4

(R)-1-(3-Phenylpropyl)-3-(3-methoxyphenyl)piperidine

The title compound was prepared by acylation of 1.0 g (5.2 mmole) of the (R)(−)-3-(3-methoxyphenyl)-piperidine from preparation 7, Part C, with 1.3 g (7.8 mmole) of 3-phenylpropionyl chloride in toluene, followed by reduction with 910 mg (24 mmole) of lithium aluminum hydride in tetrahydrofuran, using the procedure of Preparation 3. This afforded 1.9 g of an oil.

PREPARATION 5

1-(3-Phenylpropyl)-3-(4-fluoro-3-methoxyphenyl)-piperidine

The title compound was prepared by acylation of 995 mg (4.75 mmole) of the 3-(4-fluoro-3-methoxyphenyl)-piperidine from Preparation 8, Part B, with 1.2 g (7.13 mmole) of 3-phenylpropionyl chloride in toluene, followed by reduction with 831 mg (21.9 mmole) of lithium aluminum hydride in tetrahydrofuran, substantially according to the procedure of Preparation 3. This afforded 1.49 g (96% yield) of the title compound.

PREPARATION 6

1-(3-Phenylpropyl)-3-(4-fluoro-3-methoxyphenyl)-piperidine

The title compound was prepared by acylation of 209 mg (1 mmole) of the 3-(4-fluoro-3-methoxyphenyl)-piperidine from Preparation 8, Part C, with 253 mg (1.5 mmole) of 3-phenylpropionyl chloride in toluene, followed by reduction with 175 mg (4.6 mmole) of lithium aluminum hydride in tetrahydrofuran, substantially according to the procedure of Preparation 3. This afforded 305 mg (93% yield) of the title compound.

PREPARATION 7

Enantiomers of 3-(3-Methoxyphenyl)piperidine

A.

1-(2-Methoxy-2-phenyl-2-trifluoromethylacetyl)-3-(3-methoxyphenyl)piperidines

To a stirred solution of 10.4 g 54.5 mmole) of racemic 3-(3-methoxyphenyl)piperidine and 31 ml of pyridine in 140 ml of carbon tetrachloride, was added a solution of 16.5 g (65.3 mmole) of enantiomerially-pure (−)-2-methoxy-2-phenyl-2-trifluoromethylacetyl chloride in 40 ml of carbon tetrachloride. The reaction mixture was heated under reflux for 15 minutes, and then 20 ml of dimethylethylenediamine was added and the refluxing was continued for 10 minutes. The cooled reaction mixture was diluted with chloroform, and then washed sequentially with 10% hydrochloric acid, 10% sodium hydroxide, 10% hydrochloric acid and saturated sodium chloride solution. The organic solution was then evaporated in vacuo to give 25 g of crude product. This crude product was purified by rapid chromatography on silica gel to give 21.5 g of the desired mixture of diastereomers.

The mixture of diastereomers was separated by preparative high pressure liquid chromatography, eluting with hexane/ethyl acetate (10:1). This afforded:

(i) 8.48 g (38%) of the less polar diastereomer as a white solid;
(ii) 1.12 g (5%) of a mixture of diastereomers as a syrup; and
(iii) 8.85 g (40%) of the more polar diastereomer as a syrup.

B. (S)(+)-3-(3-Methoxyphenyl)piperidine

A solution of 8.4 g (0.02 mole of the less polar diastereomer from Part C, above, in 100 ml of tetrahydrofuran was added to 20.16 g (0.18 mole) of potassium t-butoxide in 400 ml of tetrahydrofuran. To this mixture was then added 1.08 ml (0.06 mole) of water, and the resulting mixture was heated under reflux for 4 days. The reaction mixture was cooled to room temperature and then the solvent was removed by evaporation in vacuo. The residue was dissolved in water and the solution was acidified with 10% hydrochloric acid. The acidified aqueous solution was washed with diethyl ether and then basified using 10% sodium hydroxide. The basified solution was extracted with ethyl acetate, and the combined extracts were washed with saturated sodium chloride solution and dried (MgSO$_4$). Evaporation of the dried ethyl acetate solution gave 3.5 g (92%) of (S)(+)-3-(3-methoxyphenyl)piperidine as an oil, [alpha]$_D^{25}$ = +4.6° (c=1; C$_2$H$_5$OH).

C. (R)(−)-3-(3-Methoxyphenyl)piperidine

The more polar diastereomer (8.8 g, 0.022 mole) from Part A, above, was hydrolyzed with 22.2 g (0.12 mole) of potassium t-butoxide and 1.2 ml (0.07 mole) of water in 550 ml of tetrahydrofuran, using the procedure of Part B above. This afforded 3.6 g (86%) of (R)(−)-3-(3-methoxyphenyl)piperidine as an oil, [alpha]$_D^{25}$ = −5.4° (c=1; C$_2$H$_5$OH).

PREPARATION 8

Enantiomers of 3-(4-Fluoro-3-methoxyphenyl)piperidine

A.

1-(2-Methoxy-2-phenyl-2-trifluoromethylacetyl)-3-(4-fluoro-3-methoxyphenyl)piperidines.

Acylation of 9.6 g (45.9 mmole) of racemic 3-(4-fluoro-3-methoxyphenyl)piperidine with 13.9 g (55.1 mmole) of enantiomerically pure (−)-2-methoxy-2-phenyl-2-trifluoromethylacetyl chloride in carbon tatrachloride, substantially according to the procedure of Preparation 7, Part A, gave the above mixture of diastereomers. This mixture was separated by preparative high pressure liquid chromatography, eluting with a 2% solution of isopropyl alcohol in hexane to give:

(i) 6.18 g (32%) of the less polar diastereomer as a white solid; and
(ii) 6.36 g (33%) of the more polar diastereomer as a white solid.

B. 3-(4-Fluoro-3-methoxyphenyl)piperidine.

The less polar diastereomer (5.74 g, 13.5 mmole) from Part A, above, was hydrolyzed with 13.6 g (121 mmole) of potassium t-butoxide and 0.73 ml (40.4 mmole) of water in 337 ml of tetrahydrofuran, substantially according to the procedure of Preparation 7, Part B. The yield was 84%.

C. 3-(4-Fluoro-3-methoxyphenyl)piperidine

The more polar diastereomer (5.93 g, 13.9 mmole) from Part A, above, was hydrolyzed with 14.0 g (125 mmole) of potassium t-butoxide and 0.75 ml 41.8 mmole) of water in 348 ml of tetrahydrofuran, substantially according to the procedure of Preparation 7, Part B. The yield was 86%.

PREPARATION 9

1-(4-Oxo-4-[4-fluorophenyl]butyl)-3-(3-methoxphenyl)-piperidine

A mixture of 1.9 g (0.01 mole) of 3-(3-methoxyphenyl)piperidine, 4.0 g (3.3 ml, 0.02 mole) of 4-oxo-4-(4-fluorophenyl)butyl chloride, 27.6 g (0.20 mole) of potassium carbonate and 75 ml of methyl isobutyl ketone was heated under reflux for ca. 40 hours. The reaction mixture was then poured onto ice-water and the resulting mixture was extracted with ethyl acetate. The combined extracts were washed with water, followed by saturated sodium chloride solution, and then they were dried and evaporated in vacuo. The residue was chromatographed on 250 ml of silica gel, eluting with chloroform/methanol (95:5). The appropriate fractions were combined and evaporated in vacuo to give 1.4 g of the title compound as an amber oil (39% yield).

PREPARATION 10

3-(3-Methoxyphenyl)piperidine

To a stirred mixture of 100 ml of 10% aqueous sodium hydroxide and 100 ml of dichloromethane was added 15 g of 3-(3-methoxyphenyl)piperidine hydrochloride. After a few minutes, the layers were separated and the organic layer was dried using potassium carbonate. Evaporation of the dichloromethane solution then afforded 12.6 g of the title compound as an oil.

PREPARATION 11

3-(4-Fluoro-3-methoxyphenyl)piperidine

To a solution of 12.3 g (60.5 mmole) of 3-(4-fluoro-3-methoxyphenyl)pyridine in a mixture of 160 ml of methanol and 20.2 ml of concentrated hydrochloric acid was added 1.6 g of platinum oxide. The resulting mixture was shaken under an atmosphere of hydrogen at an initial pressure of 50 psig for 7 hours. The reaction mixture was filtered, an additional 1 g of platinum oxide was added, and the mixture was shaken under hydrogen at a pressure of 50 psig for 2 hours. The reaction mixture was then filtered, and the bulk of the methanol was removed by evaporation in vacuo. The residual aqueous system was diluted with water, and the resulting aqueous solution was washed with ether and then basified with 100 ml of 10% sodium hydroxide. The basified mixture was extracted with diethyl ether, and the combined extracts were washed with saturated sodium chloride solution, dried (K₂CO₃) and evaporated in vacuo. This afforded 9 g (71% yield) of the title compound.

PREPARATION 12

3-(4-Fluoro-3-methoxyphenyl)pyridine

A solution of 15.6 g (76.1 mmole) of 1-bromo-4-fluoro-3-methoxybenzene in 67 ml of tetrahydrofuran was added dropwise, with stirring, under nitrogen, to 1.92 g (79.1 mmole) of dried magnesium turnings. Stirring was continued for 1 hour and then the supernatant liquid was removed to give a solution of 4-fluoro-3-methoxyphenylmagnesium bromide.

In a separate flask, 7.3 ml (76.1 mmole) of 3-bromopyridine was dissolved in 23 ml of tetrahydrofuran and 880 mg (0.76 mmole) of tetrakis-triphenylphosphine palladium was added. This latter mixture was heated to reflux, and the above Grignard solution was added dropwise, during 10 minutes, with stirring. The resulting mixture was refluxed for 1 hour and then it was stirred overnight at room temperature. The reaction mixture was diluted with 100 ml of water, followed by 100 ml of 10% hydrochloric acid, and the resulting solution was washed with dichloromethane. The aqueous phase was basified with sodium bicarbonate and then it was extracted with dichloromethane. The combined extracts were dried using potassium carbonate and evaporated in vacuo to give 12.3 g (79%) of the title compound as a reddish oil.

PREPARATION 13

1-Bromo-4-fluoro-3-methoxybenzene

To a stirred suspension of 20.8 g (0.147 mole) of 4-fluoro-3-methoxyaniline (Mulvey et al., *Tetrahedron Letters*, 16, 1419 [1978]) in 200 ml of water was added 50.2 ml of 48% hydrobromic acid. The resulting mixture was cooled to 0° C., and a solution of 11.2 g (0.162 mole) of sodium nitrite in 100 ml of water was added dropwise during 1 hour, with stirring, maintaining the temperature between 0° and 5° C. The solution of the diazonium salt thus obtained was then added to a suspension of 23.2 g (0.162 mole) of cuprous bromide in 100 ml of water which had been preheated to 75° C. The mixture was shaken thoroughly and then 251 ml of 48% hydrobromic acid was added. The resulting mixture was stirred overnight at room temperature and then it was diluted with an excess of water. The product was extracted into diethyl ether, and the extract was washed with saturated sodium chloride solution and dried (MgSO₄). Evaporation of the dried ethereal solution in vacuo afforded a black liquid, which was distilled under reduced pressure. This afforded 23 g of the title compound as a yellow liquid, b.p. 82°–85° C. (8 mm of Hg).

In like manner, 4-chloro-3-methoxyaniline (Belgian Patent No. 816,675) can be converted into 1-bromo-4-chloro-3-methoxybenzene.

I claim:
1. A compound of the formula

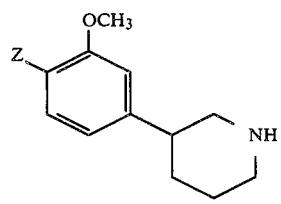

and the acid-addition salts thereof, wherein Z is fluoro or chloro.

2. A compound according to claim 1, wherein Z is fluoro.

* * * * *